US012806220B2

(12) United States Patent
Forster et al.

(10) Patent No.: US 12,806,220 B2
(45) **Date of Patent: *Nov. 24, 2026**

(54) DRUG DELIVERY SYSTEM FOR THE DELIVERY OF ANTIVIRAL AGENTS

(71) Applicant: Merck Sharp & Dohme LLC, Rahway, NJ (US)

(72) Inventors: Seth P. Forster, Fort Washington, PA (US); Stephanie Elizabeth Barrett, Cranford, NJ (US); Ryan S. Teller, Sierra Madre, CA (US); Morgan B. Giles, Weehawken, NJ (US); Athanas Koynov, Metuchen, NJ (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 1089 days.

This patent is subject to a terminal disclaimer.

(21) Appl. No.: 17/633,300

(22) PCT Filed: Aug. 11, 2020

(86) PCT No.: PCT/US2020/045693

§ 371 (c)(1),
(2) Date: Feb. 7, 2022

(87) PCT Pub. No.: WO2021/030306

PCT Pub. Date: Feb. 18, 2021

(65) Prior Publication Data

US 2022/0362277 A1 Nov. 17, 2022

Related U.S. Application Data

(60) Provisional application No. 62/885,968, filed on Aug. 13, 2019.

(51) Int. Cl.

| | |
|---|---|
| ***A61K 9/00*** | (2006.01) |
| ***A61K 9/28*** | (2006.01) |
| ***A61K 31/7076*** | (2006.01) |
| ***A61K 47/34*** | (2017.01) |
| ***A61P 31/18*** | (2006.01) |

(52) U.S. Cl.

CPC ........ *A61K 31/7076* (2013.01); *A61K 9/0024* (2013.01); *A61K 9/0092* (2013.01); *A61K 9/2853* (2013.01); *A61K 47/34* (2013.01); *A61P 31/18* (2018.01)

(58) Field of Classification Search

CPC .............. A61K 31/7076; A61K 9/0024; A61K 9/0092; A61K 9/2853; A61K 47/34; A61K 9/146; A61P 31/18

See application file for complete search history.

(56) References Cited

U.S. PATENT DOCUMENTS

| | | | | |
|---|---|---|---|---|
| 4,656,029 A | | 4/1987 | Grollier et al. | |
| 4,866,132 A | | 9/1989 | Obligin et al. | |
| 4,883,666 A | | 11/1989 | Sabel et al. | |
| 4,957,119 A | | 9/1990 | De Nijs | |
| 5,114,719 A | | 5/1992 | Sabel et al. | |
| 5,150,718 A | | 9/1992 | De Nijs | |
| 5,520,660 A | | 5/1996 | Loos et al. | |
| 5,601,835 A | | 2/1997 | Sabel et al. | |
| 6,162,236 A | | 12/2000 | Osada | |
| 6,371,094 B1 | | 4/2002 | Wagner | |
| 6,980,246 B1 | | 12/2005 | Ducourant et al. | |
| 7,087,078 B2 | | 8/2006 | Hildebrand et al. | |
| D551,759 S | | 9/2007 | Tak et al. | |
| 7,339,053 B2 | | 3/2008 | Kohgo et al. | |
| 7,378,477 B2 | | 5/2008 | Hurtevent et al. | |
| 7,553,352 B2 | | 6/2009 | Mueller et al. | |
| 8,722,037 B2 | | 5/2014 | Veenstra et al. | |
| 12,227,536 B2 | * | 2/2025 | Skomski | C07H 19/173 |
| 2001/0003297 A1 | | 6/2001 | Pedersen et al. | |
| 2001/0031940 A1 | | 10/2001 | Loos | |
| 2003/0010929 A1 | | 1/2003 | Priewe et al. | |
| 2003/0059371 A1 | | 3/2003 | Matson et al. | |
| 2003/0153983 A1 | | 8/2003 | Miller et al. | |
| 2005/0031668 A1 | | 2/2005 | Patel et al. | |
| 2005/0215512 A1 | | 9/2005 | Kohgo et al. | |
| 2008/0221510 A1 | | 9/2008 | Van Der Graaf et al. | |
| 2009/0012463 A1 | | 1/2009 | Beelen et al. | |
| 2012/0231061 A1 | * | 9/2012 | Kuzma | A61K 38/09 514/266.3 |
| 2023/0149296 A1 | * | 5/2023 | Giles | A61K 51/1203 424/422 |
| 2023/0151048 A1 | * | 5/2023 | Chang | C07H 19/06 514/46 |

FOREIGN PATENT DOCUMENTS

| | | | | |
|---|---|---|---|---|
| CN | 109893536 A | * | 6/2019 | C07H 19/173 |
| DE | 3513928 A1 | | 10/1985 | |
| DE | 29908415 U1 | | 7/1999 | |
| EP | 0073308 A1 | | 3/1983 | |
| EP | 0303306 A1 | | 2/1989 | |

(Continued)

OTHER PUBLICATIONS

Mândru al. "Characteristics of polyurethane-based sustained release membranes for drug delivery." Central European Journal of Chemistry 11 (2013): 542-553. (Year: 2013).*

Baert, L. et al., Development of a long-acting injectable formulation with nanoparticles of rilpivirine (TMC278) for HIV treatment, European Journal of Pharmaceutics and Biopharmaceutics, 2009, 502-208, 72 (3).

Barrett, Stephanie et al., Extended-Duration MK-8591-Eluting Implant as a Candidate for HIV Treatment and Prevention, Antimicrobial Agents and Chemotherapy, 2018, 1-13, vol. 62(10), e01058-18.

Gendelman, Howard E. et al., The Promise of Long Acting Antiretroviral Therapies: From Need to Manufacture, Trends Microbiol., 2019, 593-606, 27(7).

Musiime, et al., Adherence to Highly Active Antiretroviral Treatment in HIV-Infected Rwandan Women, PLOS one, 2011, 1-6, 6 (11).

(Continued)

*Primary Examiner* — Abigail Vanhorn

(74) *Attorney, Agent, or Firm* — Eric Greenwald; John C. Todaro

(57) ABSTRACT

This invention relates to novel implant drug delivery systems for long-acting delivery of antiviral drugs. These compositions are useful for the treatment or prevention of human immunodeficiency virus (HIV) infection.

24 Claims, 1 Drawing Sheet

(56) References Cited

FOREIGN PATENT DOCUMENTS

| | | | | | |
|---|---|---|---|---|---|
| EP | 0304107 | A1 | | 2/1989 | |
| EP | 0303306 | B1 | | 3/1993 | |
| EP | 0631794 | A1 | | 1/1995 | |
| EP | 0938894 | A1 | | 9/1999 | |
| EP | 0824900 | B1 | | 4/2003 | |
| EP | 0894503 | B1 | | 12/2006 | |
| EP | 1729819 | B1 | | 7/2008 | |
| GB | 2168257 | A | | 6/1986 | |
| GB | 2285981 | A | | 8/1995 | |
| JP | 1178540 | A | | 7/1989 | |
| JP | 2002360685 | A | | 12/2002 | |
| WO | 1996026682 | A1 | | 9/1996 | |
| WO | 1998058698 | A1 | | 12/1998 | |
| WO | 1999024391 | A1 | | 5/1999 | |
| WO | 1999029260 | A2 | | 6/1999 | |
| WO | 1999029260 | A3 | | 9/1999 | |
| WO | 20000012016 | A1 | | 3/2000 | |
| WO | 2001034196 | A2 | | 5/2001 | |
| WO | 2001049340 | A1 | | 7/2001 | |
| WO | 2001056646 | A1 | | 8/2001 | |
| WO | 2001068168 | A1 | | 9/2001 | |
| WO | 2001034196 | A3 | | 3/2002 | |
| WO | 2002041929 | A1 | | 5/2002 | |
| WO | 2002076525 | A1 | | 10/2002 | |
| WO | 2003051335 | A1 | | 6/2003 | |
| WO | 2004011055 | A2 | | 2/2004 | |
| WO | 2004020011 | A1 | | 3/2004 | |
| WO | 2004011055 | A3 | | 7/2004 | |
| WO | 2004089458 | A1 | | 10/2004 | |
| WO | 2005090349 | A1 | | 9/2005 | |
| WO | 2006077250 | A1 | | 7/2006 | |
| WO | 2015143712 | A1 | | 10/2015 | |
| WO | 2017027434 | A1 | | 2/2017 | |
| WO | WO-2017196697 | A1 | * | 11/2017 | ......... A61K 31/7076 |
| WO | WO-2018067882 | A1 | * | 4/2018 | ........... A61K 31/122 |
| WO | 2018191093 | A1 | | 10/2018 | |
| WO | 2020131649 | A1 | | 6/2020 | |

OTHER PUBLICATIONS

Rajoli, R.K.R. et al., Physiologically Based Pharmacokinetic Modelling to Inform Development of Intramuscular Long-Acting Nanoformulations for HIV, Clinical Pharmacokinetics, 2015, 639-650, 54 (6).

Spreen, W.R. et al., Long-acting injectable antiretrovirals for HIV treatment and prevention, Current Opinion in HIV and AIDS, 2013, 565-571, 8 (6).

Van't Klooster G. et al., Pharmacokinetics and Disposition of Rilpivirine (TMC278) Nanosuspension as a Long-Acting Injectable Antiretroviral Formulation, Antimicrobial Agents and Chemotherapy, 2010, 2042-2050, 54 (5).

* cited by examiner

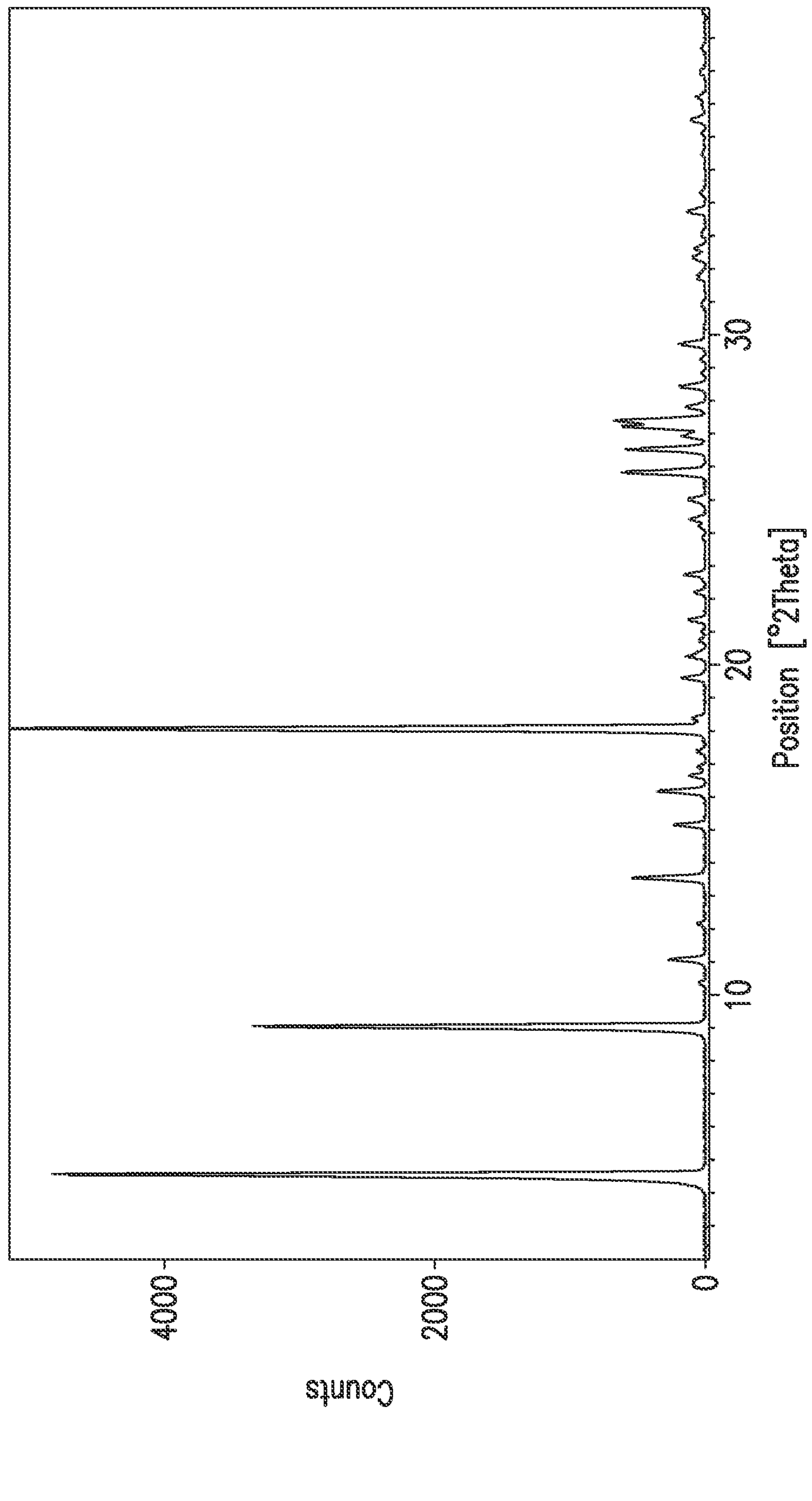
Counts
4000
2000
0
10
20
30
Position [°2Theta]

DRUG DELIVERY SYSTEM FOR THE DELIVERY OF ANTIVIRAL AGENTS

CROSS-REFERENCE TO RELATED APPLICATIONS

This application is a U.S. National Phase application under 35 U.S.C. § 371 of PCT Application No. PCT/US2020/045693, filed Aug. 11, 2020, which published as WO 2021/030306 on Feb. 18, 2021, and claims priority under 35 U.S.C. § 365(b) from U.S. Provisional Patent Application No. 62/885,968, filed Aug. 13, 2019.

BACKGROUND OF THE INVENTION

The development of highly active antiretroviral therapy (HAART) in the mid 1990's transformed the clinical care of human immunodeficiency virus (HIV) type I infection. HAART regimens have proven to be highly effective treatments, significantly decreasing HIV viral load in HIV-infected patients, thereby slowing the evolution of the illness and reducing HIV-related morbidity and mortality. Yet, the treatment success of HAART is directly related to adherence to the regimen by the patient. Unless appropriate levels of the antiretroviral drug combinations are maintained in the blood, viral mutations will develop, leading to therapy resistance and cross-resistances to molecules of the same therapeutic class, thus placing the long-term efficacy of treatments at risk. Various clinical studies have shown a decline in treatment effectiveness with relatively small lapses in adherence. A study by Musiime found that 81% of patients with more than 95% adherence demonstrated viral suppression, while only 50% of patients who were 80-90% adherent were successful. See, Musiime, S., et al., Adherence to Highly Active Antiretroviral Treatment in HIV-Infected Rwandan Women. *PLOS one* 2011, 6, (11), 1-6. Remarkably, only 6% of patients that were less than 70% adherent showed improvements in viral markers. Thus, low adherence is a leading cause of therapeutic failure in treatment of HIV-1 infection.

Nonetheless, adherence rates to the HAART regimens continue to be far from optimal. Various characteristics of HAART make adherence particularly difficult. Therapeutic regimens are complex, requiring multiple drugs to be taken daily, often at different times of the day, and many with strict requirements on food intake. Many HAART medications also have unpleasant side effects, including nausea, diarrhea, headache, and peripheral neuropathy. Social and psychological factors can also negatively impact adherence. Patients report that forgetfulness, lifestyle factors, including fear of being identified as HIV-positive, and therapy fatigue over life-long duration of treatment all contribute to adherence lapses.

New HIV treatment interventions aim to improve adherence by reducing the complexity of treatments, the frequency of the dosages, and/or the side effects of the medications. Long-acting injectable (LAI) drug formulations that permit less frequent dosing, on the order of a month or longer, are an increasingly attractive option to address adherence challenges. However, the majority of approved and investigational antiretroviral agents are not well suited for reformulation as long-acting injectable products. In large part, this is due to suboptimal physicochemical properties limiting their formulation as conventional drug suspensions, as well as insufficient antiviral potency resulting in high monthly dosing requirements. Even for cabotegravir or rilpivirine, two drugs being studied as long-acting injectible formulations, large injection volumes and multiple injections are required to achieve pharmacokinetic profiles supportive of monthly dosing. See, e.g., Spreen, W. R., et al., Long-acting injectable antiretrovirals for HIV treatment and prevention. *Current Opinion in Hiv and Aids* 2013, 8, (6), 565-571; Rajoli, R. K. R., et al., Physiologically Based Pharmacokinetic Modelling to Inform Development of Intramuscular Long-Acting Nanoformulations for HIV. *Clinical Pharmacokinetics* 2015, 54, (6), 639-650; Baert, L., et al., Development of a long-acting injectable formulation with nanoparticles of rilpivirine (TMC278) for HIV treatment. *European Journal of Pharmaceutics and Biopharmaceutics* 2009, 72, (3), 502-508; Van't Klooster, G., et al., Pharmacokinetics and Disposition of Rilpivirine (TMC278) Nanosuspension as a Long-Acting Injectable Antiretroviral Formulation. *Antimicrobial Agents and Chemotherapy* 2010, 54, (5), 2042-2050. Thus, novel formulation approaches capable of delivering extended-duration pharmacokinetic characteristics for molecules of diverse physicochemical properties at practical injection volumes and with a limited number of injections are highly desirable.

SUMMARY OF THE INVENTION

This invention relates to novel implant drug delivery systems for long-acting delivery of antiviral drugs. These compositions are useful for the treatment or prevention of human immunodeficiency virus (HIV) infection.

BRIEF DESCRIPTION OF THE DRAWINGS

The FIGURE is a graph of a Powder X-Ray Diffraction ("PXRD") pattern of anhydrate crystalline Form 4 of EFdA, generated using the equipment and methods described herein. The graph plots the intensity of the peaks as defined by counts per second versus the 10 diffraction angle 2 theta (2Θ) in degrees.

DETAILED DESCRIPTION OF THE INVENTION

This invention relates to novel implant drug delivery systems for long-acting delivery of antiviral drugs. The novel implant drug delivery systems comprise a polymer and an antiviral agent. These implant drug delivery systems are useful for the treatment or prevention of human immunodeficiency virus (HIV) infection. The invention further relates to methods of treating and preventing HIV infection with the novel implant drug delivery systems described herein.

The novel implant delivery systems of the invention comprise a biocompatible nonerodible polymer to generate monolithic matrices with dispersed or dissolved drug. The chemical properties of the polymer matrices are tuned to achieve a range of drug release characteristics, offering the opportunity to extend duration of dosing. In an embodiment of the invention, the novel implant delivery systems are compatible with molecules having a broad spectrum of physicochemical properties, including those of high aqueous solubility or amorphous phases which are unsuitable to formulation as solid drug suspensions.

Specifically, this invention relates to novel implant drug delivery systems comprising:

(a) a core comprising a biocompatible nonerodible polymer and 4'-ethynyl-2-fluoro-2'-deoxyadenosine anhydrate, which is present in the core between 1% to 60% by weight, and (b) a biocompatible nonerodible diffusional barrier comprising a polymer, wherein said diffusional barrier has a thickness between 50 μm and 300 μm, wherein said implant drug delivery system is implanted subdermally and 4'-ethynyl-2-fluoro-2'-deoxyadenosine anhydrate is continually released in vivo at a rate resulting in a plasma concentration of 4'-ethynyl-2-fluoro-2'-deoxyadenosine between 0.02 ng/mL and 300.0 ng/mL for a period of six months to thirty-six months. These implant delivery systems are desired and useful for prophylaxis and/or treatment of HIV infection from both compliance and convenience standpoints.

The invention also relates to novel implant drug delivery systems comprising:

(a) a core comprising a biocompatible nonerodible polymer and 4'-ethynyl-2-fluoro-2'-deoxyadenosine, which is present in the core between 1% to 60% by weight, and (b) a biocompatible nonerodible diffusional barrier comprising a polymer, wherein said diffusional barrier has a thickness between 50 μm and 300 μm, wherein said implant drug delivery system is implanted subdermally and 4'-ethynyl-2-fluoro-2'-deoxyadenosine is continually released in vivo at a rate resulting in a plasma concentration of 4'-ethynyl-2-fluoro-2'-deoxyadenosine between 0.02 ng/mL and 300.0 ng/mL for a period of six months to thirty-six months. These implant delivery systems are desired and useful for prophylaxis and/or treatment of HIV infection from both compliance and convenience standpoints.

In an embodiment, the instant invention also relates to implant drug delivery systems comprising:

(a) a core comprising a biocompatible nonerodible polymer and 4'-ethynyl-2-fluoro-2'-deoxyadenosine anhydrate, which is present in the core between 1% to 60% by weight, and (b) a biocompatible nonerodible diffusional barrier comprising a polymer, wherein said diffusional barrier has a thickness between 50 μm and 300 μm, wherein said 4'-ethynyl-2-fluoro-2'-deoxyadenosine anhydrate has an in vitro release rate of 0.03 to 0.07 mg/day when measured between one and six months.

In an embodiment, the instant invention also relates to implant drug delivery systems comprising:

(a) a core comprising a biocompatible nonerodible polymer and 4'-ethynyl-2-fluoro-2'-deoxyadenosine anhydrate, which is present in the core between 1% to 60% by weight, and (b) a biocompatible nonerodible diffusional barrier comprising a polymer, wherein said diffusional barrier has a thickness between 50 μm and 300 μm, wherein said 4'-ethynyl-2-fluoro-2'-deoxyadenosine anhydrate has an in vitro release rate of 0.07 mg/day when measured at day 30.

In another embodiment, the instant invention also relates to implant drug delivery systems comprising:

(a) a core comprising a biocompatible nonerodible polymer and 4'-ethynyl-2-fluoro-2'-deoxyadenosine anhydrate, which is present in the core between 1% to 60% by weight, and (b) a biocompatible nonerodible diffusional barrier comprising a polymer, wherein said diffusional barrier has a thickness between 50 μm and 300 μm, wherein said 4'-ethynyl-2-fluoro-2'-deoxyadenosine anhydrate has an in vitro release rate of 0.04 mg/day when measured at day 60.

In a further embodiment, the instant invention also relates to implant drug delivery systems comprising:

(a) a core comprising a biocompatible nonerodible polymer and 4'-ethynyl-2-fluoro-2'-deoxyadenosine anhydrate, which is present in the core between 1% to 60% by weight, and (b) a biocompatible nonerodible diffusional barrier comprising a polymer, wherein said diffusional barrier has a thickness between 50 μm and 300 μm, wherein said 4'-ethynyl-2-fluoro-2'-deoxyadenosine anhydrate has an in vitro release rate of 0.03 mg/day when measured at day 90.

In a further embodiment, the instant invention also relates to implant drug delivery systems comprising:

(a) a core comprising a biocompatible nonerodible polymer and 4'-ethynyl-2-fluoro-2'-deoxyadenosine anhydrate, which is present in the core between 1% to 60% by weight, and (b) a biocompatible nonerodible diffusional barrier comprising a polymer, wherein said diffusional barrier has a thickness between 50 μm and 300 μm, wherein said 4'-ethynyl-2-fluoro-2'-deoxyadenosine anhydrate has an in vitro release rate of 0.03 mg/day when measured after six months.

As used herein, the term "biocompatible nonerodible polymer" refers to polymeric materials that are sufficiently resistant to degradation (both chemical and physical) in the presence of biological systems. Biocompatible nonerodible polymers are sufficiently resistant to chemical and/or physical destruction by the environment of use such that the polymer remains essentially intact throughout the release period. The nonerodable polymer is generally hydrophobic so that it retains its integrity for a suitable period of time when placed in an aqueous environment, such as the body of a mammal, and stable enough to be stored for an extended period before use. The nonerodible polymers useful in the invention remain intact in vivo for extended periods of time, typically months or years. Drug molecules encapsulated in the polymer are released over time via diffusion through channels and pores in a sustained manner. The release rate can be altered by modifying the percent drug loading, porosity of the polymer, structure of the implantable device, or hydrophobicity of the polymer, or by adding a coating to the exterior of the implantable device.

Accordingly, any polymer that cannot be absorbed by the body can be used to manufacture the implant drug delivery systems of the instant invention. Biocompatible nonerodible polymers of the instant invention include, but are not limited to, ethylene vinylacetate copolymer (EVA), poly(urethane), silicone, crosslinked poly(vinyl alcohol), poly(hydroxy ethylmethacrylate), acyl substituted cellulose acetates, partially hydrolyzed alkylene-vinyl acetate copolymers, completely hydrolyzed alkylene-vinyl acetate copolymers, unplasticized polyvinyl chloride, crosslinked homopolymers of polyvinyl acetate, crosslinked copolymers of polyvinyl acetate, crosslinked polyesters of acrylic acid, crosslinked polyesters of methacrylic acid, polyvinyl alkyl ethers, polyvinyl fluoride, polycarbonate, polyamide, polysulphones, styrene acrylonitrile copolymers, crosslinked poly(ethylene oxide), poly(alkylenes), poly(vinyl imidazole), poly(esters), poly(ethylene terephthalate), polyphosphazenes, chlorosulphonated polylefins, and combinations thereof. In a class of the invention, the biocompatible nonerodible polymer is poly(urethane).

In a class of the invention, the biocompatible nonerodible polymer in the core and the polymer of the biocompatible nonerodable diffusional barrier are the same polymer. In a subclass of the invention, the biocompatible nonerodible polymer in the core and the polymer of the biocompatible nonerodable diffusional barrier are both poly(urethane).

As used herein, the term "diffusional barrier" refers to a barrier that is permeable to the drug and is placed over at least a portion of the core to further regulate the rate of release. For example, a coating of biocompatible nonerodible polymeric material, e.g., poly(urethane), or a coating of a biocompatible nonerodible polymeric material with a lower drug loading than the remainder of the implant delivery system, may be used. The diffusional barrier may be formed, for example, by co-extrusion with the core, by injection molding, or other ways known in the art. The diffusional barriers of the instant invention can also be referred to as a "biocompatible nonerodable diffusional barrier" or a "skin."

The diffusional barriers of the instant invention comprise hydrophilic polymers or hydrophobic polymers with a soluble filler.

Suitable polymers for use in the diffusional barriers of the instant invention include, but are not limited to, ethylene vinylacetate copolymer (EVA), silicone, crosslinked poly (vinyl alcohol), unplasticized polyvinyl chloride, crosslinked homopolymers of polyvinyl acetate, crosslinked copolymers of polyvinyl acetate, crosslinked polyesters of acrylic acid, crosslinked polyesters of methacrylic acid, polyvinyl alkyl ethers, polyvinyl fluoride, polycarbonate, polyamide, polysulphones, styrene acrylonitrile copolymers, crosslinked poly(ethylene oxide), poly(alkylenes), poly(vinyl imidazole), poly(ethylene terephthalate), poly(urethane), poly(hydroxy ethylmethacrylate), acyl substituted cellulose acetates, partially hydrolyzed alkylene-vinyl acetate copolymers, completely hydrolyzed alkylene-vinyl acetate copolymers, poly(esters), polyphosphazenes, chlorosulphonated polylefins, and combinations thereof. In a class of the invention, the diffusional barrier is selected from the group consisting of poly(urethane), poly(hydroxy ethylmethacrylate), acyl substituted cellulose acetates, partially hydrolyzed alkylene-vinyl acetate copolymers, completely hydrolyzed alkylene-vinyl acetate copolymers, poly(esters), polyphosphazenes, chlorosulphonated polylefins, and combinations thereof. In a subclass of the invention, the diffusional barrier comprises poly(urethane). In a further subclass of the invention, the poly(urethane) has a water uptake of between 1% and 100% by weight. In a further subclass of the invention, the poly(urethane) has a water uptake of between 1% and 20% by weight.

In an embodiment of the invention, the diffusional barrier has a thickness between 50 μm and 300 μm. In a class of the embodiment, the diffusional barrier has a thickness between 50 μm and 200 μm. In a subclass of the embodiment, the diffusional barrier has a thickness between 100 μm and 200 μm.

In an embodiment of the invention, the diffusional barrier contains an antiviral drug. In a class of the embodiment, the diffusional barrier comprises 4'-ethynyl-2-fluoro-2'-deoxyadenosine anyhdrate. In another class of the embodiment, the diffusional barrier comprises 4'-ethynyl-2-fluoro-2'-deoxyadenosine.

As used herein, the term "dispersed or dissolved in the biocompatible nonerodible polymer" refers to the drug and polymer being mixed and then hot-melt extruded.

As used herein, the term "continually released" refers to the drug being released from the biocompatible nonerodible polymer at a sufficient rate over extended periods of time to achieve a desired therapeutic or prophylactic concentration. The implant drug delivery systems of the instant invention generally exhibit linear release kinetics for the drug in vivo, sometimes after an initial burst. The 4'-ethynyl-2-fluoro-2'-deoxyadenosine anyhdrate in the core converts to 4'-ethynyl-2-fluoro-2'-deoxyadenosine monohydrate once it is released and becomes exposed to aqueous media, such as blood and plasma. When measuring the concentration in vivo, it is the dissolved form, 4'-ethynyl-2-fluoro-2'-deoxyadenosine, that is measured.

The terms "treating" or "treatment" as used herein with respect to an HIV viral infection or AIDS, includes inhibiting the severity of HIV infection or AIDS, i.e., arresting or reducing the development of the HIV infection or AIDS or its clinical symptoms; or relieving the HIV infection or AIDS, i.e., causing regression of the severity of HIV infection or AIDS or its clinical symptoms.

The terms "preventing," or "prohylaxis," as used herein with respect to an HIV viral infection or AIDS, refers to reducing the likelihood or severity of HIV infection or AIDS.

Optionally, the novel implant delivery systems of the instant invention can further comprise a radiopaque component. The radiopaque component will cause the implant to be X-ray visible. The radiopaque component can be any such element known in the art, such as barium sulfate, titanium dioxide, bismuth oxide, bismuth oxychloride, bismuth trioxide, tantalum, tungsten or platinum. In a specific embodiment, the radiopaque component is barium sulfate.

In one embodiment, the radiopaque material is 1% to 30% by weight. In another embodiment, the radiopaque material is 1% to 20% by weight. In another embodiment, the radiopaque material is 4% to 25% by weight. In further embodiment, the radiopaque material is 6% to 20% by weight. In another embodiment, the radiopaque material is 4% to 15% by weight. In another embodiment, the radiopaque material is about 8% to 15% by weight.

The radiopaque material does not affect the release of 4'-ethynyl-2-fluoro-2'-deoxyadenosine anhydrate from the implant.

The novel implant delivery systems of the invention comprise antiviral agents. Suitable antiviral agents include anti-HIV agents. In an embodiment of the invention, the antiviral agent is administered as a monotherapy. In another embodiment of the invention, two or more antiviral agents are administered in combination.

An "anti-HIV agent" is any agent which is directly or indirectly effective in the inhibition of HIV reverse transcriptase or another enzyme required for HIV replication or infection, or the prophylaxis of HIV infection, and/or the treatment, prophylaxis or delay in the onset or progression of AIDS. It is understood that an anti-HIV agent is effective in treating, preventing, or delaying the onset or progression of HIV infection or AIDS and/or diseases or conditions arising therefrom or associated therewith. Suitable anti-viral agents for use in implant drug delivery systems described herein include, for example, those listed in Table A as follows:

Antiviral Agents for Preventing HIV Infection or AIDS

| Name | Type |
|---|---|
| abacavir, ABC, Ziagen ® | nRTI |
| abacavir + lamivudine, Epzicom ® | nRTI |
| abacavir + lamivudine + zidovudine, Trizivir ® | nRTI |
| amprenavir, Agenerase ® | PI |
| atazanavir, Reyataz ® | PI |
| AZT, zidovudine, azidothymidine, Retrovir ® | nRTI |
| Capravirine | nnRTI |
| darunavir, Prezista ® | PI |
| ddC, zalcitabine, dideoxycytidine, Hivid ® | nRTI |
| ddI, didanosine, dideoxyinosine, Videx ® | nRTI |
| ddI (enteric coated), Videx EC ® | nRTI |
| delavirdine, DLV, Rescriptor ® | nnRTI |
| Doravirine, Pifeltro ™ | nnRTI |
| doravirine + lamivudine + tenofovir D F, Delstrigo ™ | nnRTI + nRTI |
| efavirenz, EFV, Sustiva ®, Stocrin ® | nnRTI |
| efavirenz + emtricitabine + tenofovir DF, Atripla ® | nnRTI + nRTI |
| emtricitabine, FTC, Emtriva ® | nRTI |
| emtricitabine + tenofovir DF, Truvada ® | nRTI |
| emvirine, Coactinon ® | nnRTI |
| enfuvirtide, Fuzeon ® | FI |
| enteric coated didanosine, Videx EC ® | nRTI |
| etravirine, TMC-125 | nnRTI |
| fosamprenavir calcium, Lexiva ® | PI |
| GS-6207 | CI |
| indinavir, Crixivan ® | PI |
| islatravir (EFdA or 4'-ethynyl-2-fluoro-2'-deoxyadenosine) | nRTTI |
| lamivudine, 3TC, Epivir ® | nRTI |
| lamivudine + zidovudine, Combivir ® | nRTI |
| Lopinavir | PI |
| lopinavir + ritonavir, Kaletra ® | PI |
| maraviroc, Selzentry ® | EI |
| nelfinavir, Viracept ® | PI |
| nevirapine, NVP, Viramune ® | nnRTI |
| PPL-100 (also known as PL-462) (Ambrilia) | PI |
| raltegravir, Isentress ™ | InI |
| (S)-2-(3-chloro-4-fluorobenzyl)-8-ethyl-10-hydroxy-N,6-dimethyl- | InI |
| ritonavir, Norvir ® | PI |
| saquinavir, Invirase ®, Fortovase ® | PI |
| stavudine, d4T, didehydrodeoxythymidine, Zerit ® | nRTI |
| tenofovir DF (DF = disoproxil fumarate), TDF, Viread ® | nRTI |
| Tenofovir, hexadecyloxypropyl (CMX-157) | nRTI |
| tipranavir, Aptivus ® | PI |
| Vicriviroc | EI |

CI = capsid inhibitor; EI = entry inhibitor; FI = fusion inhibitor; InI = integrase inhibitor; PI = protease inhibitor; nRTI = nucleoside reverse transcriptase inhibitor; nnRTI = non-nucleoside reverse transcriptase inhibitor; nRTTI = nucleoside reverse transcriptase translocation inhibitor.

Some of the drugs listed in the table can be used in a salt form; e.g., abacavir sulfate, delavirdine mesylate, indinavir sulfate, atazanavir sulfate, nelfinavir mesylate, saquinavir mesylate.

In certain embodiments the antiviral agents in the implant drug delivery systems described herein are employed in their conventional dosage ranges and regimens as reported in the art, including, for example, the dosages described in editions of the *Physicians' Desk Reference*, such as the 63rd edition (2009) and earlier editions. In other embodiments, the antiviral agents in the implant drug delivery systems described herein are employed in lower than their conventional dosage ranges. In other embodiments, the antiviral agents in the implant drug delivery systems described herein are employed in higher than their conventional dosage ranges.

In an embodiment of the invention, the antiviral agent can be an entry inhibitor; fusion inhibitor; integrase inhibitor; protease inhibitor; nucleoside reverse transcriptase inhibitor; or non-nucleoside reverse transcriptase inhibitor. In a class of the invention, the antiviral agent is a nucleoside reverse transcriptase inhibitor.

In an embodiment of the invention, the antiviral agent is a nucleoside reverse transciptase translocation inhibitor (NRTTI). In a class of the invention, the NRTTI is 4'-ethynyl-2-fluoro-2'-deoxyadenosine. In a subclass of the invention, the NRTTI is 4'-ethynyl-2-fluoro-2'-deoxyadenosine anhydrate.

4'-ethynyl-2-fluoro-2'-deoxyadenosine is also known as islatravir and EFdA, and has the following chemical structure:

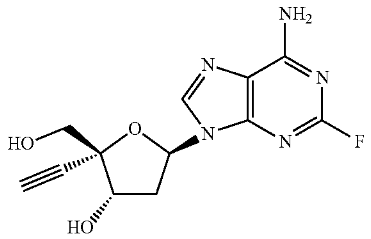 [SMILES: C#C[C@]1(CO)O[C@@H](n2cnc3c(N)nc(F)nc32)C[C@@H]1O]

Production of and the ability of 4'-ethynyl-2-fluoro-2'-deoxyadenosine to inhibit HIV reverse transcriptase are described in PCT International Application WO2005090349, published on Sep. 29, 2005, and US Patent Application Publication No. 2005/0215512, published on Sep. 29, 2005, both to Yamasa Corporation, both of which are hereby incorporated by reference in their entirety.

The PXRD pattern for an anhydrate crystalline form of EFdA is displayed in The FIGURE and described in copending application International Application Serial No. PCT/US19/066436, filed Dec. 16, 2019, which is hereby incorporated by reference in its entirety. Thus, in an aspect of this disclosure, there is provided an anhydrate crystalline form of EFdA characterized by a powder x-ray diffraction pattern substantially as shown in The FIGURE. Peak locations (on the 2 theta x-axis) consistent with these profiles are displayed in the table below (+/−0.2° 2 theta). The locations of these PXRD peaks are characteristic of an anhydrate crystalline form of EFdA. Thus, in another aspect, an anhydrate crystalline form of EFdA is characterized by a powder x-ray diffraction pattern having each of the peak positions listed in the table below, +/−0.2° 2-theta.

| Diagnostic Peak Set | Peak Location [°2Th.] (+/−0.2° 2-theta) | d-spacing [Å] | Relative intensity [%] | Peak No. |
|---|---|---|---|---|
| 2 | 4.48 | 19.73 | 68.9 | 1 |
| 3 | 8.99 | 9.87 | 48.6 | 2 |
| 4 | 10.16 | 8.71 | 15.9 | 3 |
| 3 | 10.39 | 8.51 | 46.0 | 4 |
| 1 | 11.79 | 7.50 | 54.2 | 5 |
| 1 | 12.39 | 7.14 | 36.5 | 6 |
| 1 | 14.70 | 6.03 | 41.2 | 7 |
| 1 | 15.51 | 5.71 | 36.3 | 8 |
| 4 | 15.98 | 5.55 | 17.1 | 9 |
| 4 | 16.64 | 5.33 | 20.1 | 10 |
| 3 | 16.88 | 5.25 | 59.2 | 11 |
| | 17.39 | 5.10 | 13.6 | 12 |
| 2 | 18.09 | 4.91 | 60.3 | 13 |
| | 18.30 | 4.85 | 16.3 | 14 |
| 3 | 20.16 | 4.40 | 67.1 | 15 |
| | 21.69 | 4.10 | 13.4 | 16 |
| 4 | 24.96 | 3.57 | 43.7 | 17 |
| 2 | 25.81 | 3.45 | 100.0 | 18 |

-continued

| Diagnostic Peak Set | Peak Location [°2Th.] (+/−0.2° 2-theta) | d-spacing [Å] | Relative intensity [%] | Peak No. |
|---|---|---|---|---|
| 2 | 27.42 | 3.25 | 92.7 | 19 |
| | 29.69 | 3.01 | 13.0 | 20 |

Thus, in one aspect, an anhydrate crystalline form of EFdA is characterized by a powder x-ray diffraction pattern having each of the peak locations listed in the table above, +/−0.2° 2-theta.

In another aspect, an anhydrate crystalline form of EFdA is characterized by a powder x-ray diffraction pattern comprising two or more of the 2-theta values listed in the table above, +/−0.2° 2-theta.

In another aspect, an anhydrate crystalline form of EFdA is characterized by a powder x-ray diffraction pattern comprising three or more of the 2-theta values listed in the table above, +/−0.2° 2-theta.

In another aspect, an anhydrate crystalline form of EFdA is characterized by a powder x-ray diffraction pattern comprising four or more of the 2-theta values listed in the table above, +/−0.2° 2-theta.

In another aspect, an anhydrate crystalline form of EFdA is characterized by a powder x-ray diffraction pattern comprising six or more of the 2-theta values listed in the table above, +/−0.2° 2-theta.

In another aspect, an anhydrate crystalline form of EFdA is characterized by a powder x-ray diffraction pattern comprising nine or more of the 2-theta values listed in the table above, +/−0.2° 2-theta.

In another aspect, an anhydrate crystalline form of EFdA is characterized by a powder x-ray diffraction pattern comprising twelve or more of the 2-theta values listed in the table above, +/−0.2° 2-theta.

In a further aspect, the PXRD peak locations displayed in the table above and/or The FIGURE most characteristic of an anhydrate crystalline form of EFdA can be selected and grouped as "diagnostic peak sets" to conveniently distinguish this crystalline form from others. Selections of such characteristic peaks are set out in the table above in the column labeled Diagnostic Peak Set.

Thus, in another aspect, there is provided an anhydrate crystalline form of EFdA characterized by a powder x-ray diffraction pattern comprising each of the 2-theta values listed in Diagnostic Peak Set 1 in the table above, +/−0.2° 2-theta.

In another aspect, there is provided an anhydrate crystalline form of EFdA characterized by a powder x-ray diffraction pattern comprising each of the 2-theta values listed in Diagnostic Peak Set 2 in the table above, +/−0.2° 2-theta.

In another aspect, there is provided an anhydrate crystalline form of EFdA characterized by a powder x-ray diffraction pattern comprising each of the 2-theta values listed in Diagnostic Peak Set 3 in the table above, +/−0.2° 2-theta.

In another aspect, there is provided an anhydrate crystalline form of EFdA characterized by a powder x-ray diffraction pattern comprising each of the 2-theta values listed in Diagnostic Peak Set 4 in the table above, +/−0.2° 2-theta.

In another aspect, there is provided an anhydrate crystalline form of EFdA characterized by a powder x-ray diffraction pattern comprising each of the 2-theta values listed in Diagnostic Peak Set 1 and any one or more of Diagnostic Peak Set 2, Diagnostic Peak Set 3, and/or Diagnostic Peak Set 4 in the table above, +/−0.2° 2-theta.

In another aspect, there is provided an anhydrate crystalline Form of EFdA characterized by a powder x-ray diffraction pattern comprising each of the 2-theta values listed in Diagnostic Peak Set 2 and any one or more of Diagnostic Peak Set 1, Diagnostic Peak Set 3, and/or Diagnostic Peak Set 4 in the table above, +/−0.2° 2-theta.

In another aspect, there is provided an anhydrate crystalline form of EFdA characterized by a powder x-ray diffraction pattern comprising each of the 2-theta values listed in Diagnostic Peak Set 3 and any one or more of Diagnostic Peak Set 1, Diagnostic Peak Set 2, and/or Diagnostic Peak Set 4 in the table above, +/−0.2° 2-theta.

In another aspect, there is provided an anhydrate crystalline form of EFdA characterized by a powder x-ray diffraction pattern comprising each of the 2-theta values listed in Diagnostic Peak Set 4 and any one or more of Diagnostic Peak Set 1, Diagnostic Peak Set 2, and/or Diagnostic Peak Set 3 in the table above, +/−0.2° 2-theta.

In another aspect, an anhydrate crystalline form of EFdA is characterized by the PXRD spectrum as shown in The FIGURE.

In yet another aspect, anhydrate crystalline form of EFdA is characterized by the above described PXRD characteristic peaks and/or the data shown in The FIGURE, alone or in combination with any of the other characterizations of the anhydrate form of EFdA described herein.

Powder X-ray Diffraction data were acquired on a Panalytical X-pert Pro PW3040 System configured in the 20 Bragg-Brentano configuration and equipped with a Cu radiation source with monochromatization to Kα achieved using a Nickel filter. A fixed slit optical configuration was employed for data acquisition. Data were acquired between 2 and 40° 2θ. Samples were prepared by gently pressing powdered sample onto a shallow cavity zero background silicon holder. The counting time for powder X-Ray Diffraction (PXRD) was 50.800 seconds using EFdA powder samples.

Those skilled in the art will recognize that the measurements of the XRD peak locations for a given crystalline form of the same compound will vary within a margin of error. The margin of error for the 2-theta values measured as described herein is typically +/−0.2° 2-theta. Variability can depend on such factors as the system, methodology, sample, and 30 conditions used for measurement. As will also be appreciated by the skilled crystallographer, the intensities of the various peaks reported in the figures herein may vary due to a number of factors such as orientation effects of crystals in the x-ray beam, the purity of the material being analyzed, and/or the degree of crystallinity of the sample. The skilled crystallographer also will appreciate that measurements using a different wavelength will result in different shifts according to the Bragg-Brentano equation. Such further XRD patterns generated by use of alternative wavelengths are considered to be alternative representations of the XRD patterns of the crystalline material of the present disclosure and as such are within the scope 5 of the present disclosure.

The PXRD pattern shown in The FIGURE was generated using the equipment and procedures described above. The intensity of the peaks (y-axis is in counts per second) for each PXRD pattern is plotted versus the 2 theta angle (x-axis is in degrees 2 theta). In addition, the data were plotted with detector counts normalized for the collection time per step versus the 2 theta angle.

In an embodiment of the implant drug delivery system described herein, the antiviral agent is present in the core at 1%-60% by weight. In another embodiment of the implant drug delivery system described herein, the antiviral agent is present in the core at 10%-60% by weight. In other embodiments, the antiviral agent is present in the core at about 40% by weight or at about 60% by weight. In a class of the embodiment of the implant drug delivery system described herein, 4'-ethynyl-2-fluoro-2'-deoxyadenosine anhydrate is present in the core at 1%-60% by weight. In a subclass of the embodiment of the implant drug delivery system described herein, 4'-ethynyl-2-fluoro-2'-deoxyadenosine anhydrate is present in the core at 10%-60% by weight. In another subclass of the embodiment of the implant drug delivery system described herein, 4'-ethynyl-2-fluoro-2'-deoxyadenosine anhydrate is present in the core at 15% to 40% by weight. In another subclass of the embodiment of the implant drug delivery system described herein, 4'-ethynyl-2-fluoro-2'-deoxyadenosine anhydrate is present in the core at about 40% by weight. In another subclass of the embodiment of the implant drug delivery system described herein, 4'-ethynyl-2-fluoro-2'-deoxyadenosine anhydrate is present in the core at about 60% by weight.

The implant drug delivery systems of the instant invention may be produced using an extrusion process, wherein ground biocompatible, nonerodible polymer is blended with the antiviral agent, melted and extruded into rod-shaped structures. Rods are cut into individual implantable devices of the desired length, packaged and sterilized prior to use. Other methods for encapsulating therapeutic compounds in implantable polymeric, nonerodible matrices are known to those of skill in the art. Such methods include solvent casting (see U.S. Pat. Nos. 4,883,666, 5,114,719 and 5,601,835). One of skill in the art would be able to readily determine an appropriate method of preparing such an implant drug delivery system, depending on the shape, size, drug loading, and release kinetics desired for a particular type of patient or clinical application.

The implant drug delivery systems of the instant invention may be produced using a co-extrusion process of the core and the biocompatible nonerodable diffusional barrier. In an embodiment of the invention, the core and the biocompatible nonerodible diffusional barrier are prepared by co-extrusion, and the co-extrusion is carried out at a temperature between 130 °C and 190 °C. In a class of the invention, the biocompatible nonerodible polymer core and the biocompatible nonerodible diffusional barrier are prepared by co-extrusion, and the co-extrusion is carried out at a temperature between 130 °C and 160 °C.

The size and shape of the implant drug delivery systems may be modified to achieve a desired overall dosage. The implant drug delivery systems of the instant invention are often about 0.5 cm to about 10 cm in length. In an embodiment of the invention, the implant drug delivery systems are about 1.5 cm to about 5 cm in length. In a class of the embodiment, the implant drug delivery systems are about 2 cm to about 5 cm in length. In a subclass of the embodiment, the implant drug delivery systems are about 2 cm to about 4 cm in length. The implant drug delivery systems of the instant invention are often about 0.5 mm to about 7 mm in diameter. In an embodiment of the invention, the implant drug delivery systems are about 1.5 mm to about 5 mm in diameter. In a class of the embodiment, the implant drug delivery systems are about 2 mm to about 5 mm in diameter. In a subclass of the embodiment, the implant drug delivery systems are about 2 mm to about 4 mm in diameter.

The implant drug delivery systems described herein are capable of releasing 4'-ethynyl-2-fluoro-2'-deoxyadenosine anhydrate over a period of 21 days, 28 days, 31 days, 4 weeks, 6 weeks, 8 weeks, 12 weeks, one month, two months, three months, four months, five months, six months, seven months, eight months, nine months, ten months, eleven months, twelve months, eighteen months, twenty-four months or thirty-six months at an average rate of between 0.02-8.0 ng per day. In an embodiment of the invention, the 4'-ethynyl-2-fluoro-2'-deoxyadenosine anhydrate is released at therapeutic concentrations for a duration from between six months and thirty-six months. In a class of the embodiment, the 4'-ethynyl-2-fluoro-2'-deoxyadenosine anhydrate is released at therapeutic concentrations for a duration from between six months and twelve months. In another class of the embodiment, the 4'-ethynyl-2-fluoro-2'-deoxyadenosine anhydrate is released at therapeutic concentrations for a duration from between twenty-four months and thirty-six months. In an embodiment of the invention, the 4'-ethynyl-2-fluoro-2'-deoxyadenosine anhydrate is released at prophylactic concentrations for a duration from between six months and thirty-six months. In a class of the embodiment, the 4'-ethynyl-2-fluoro-2'-deoxyadenosine anhydrate is released at prophylactic concentrations for a duration from between six months and twelve months. In another class of the embodiment, the 4'-ethynyl-2-fluoro-2'-deoxyadenosine anhydrate is released at prophylactic concentrations for a duration from between twenty-dour months and thirty-six months.

One or more implants can be used to achieve the desired therapeutic or prophylactic dose. In an embodiment of the invention, one or more implants can be used to achieve the therapeutic dose for durations of up to 1 year. In another embodiment of the invention, one or more implants can be used to achieve the therapeutic dose for durations of up to 2 years.

The implant drug delivery systems described herein are capable of releasing 4'-ethynyl-2-fluoro-2'-deoxyadenosine anhydrate resulting in a plasma concentration of 4'-ethynyl-2-fluoro-2'-deoxyadenosine between 0.02-300 ng/mL per day. In an embodiment of the invention, the implant drug delivery systems described herein are capable of releasing 4'-ethynyl-2-fluoro-2'-deoxyadenosine anhydrate resulting in a plasma concentration of 4'-ethynyl-2-fluoro-2'-deoxyadenosine between 0.02-30.0 ng/mL per day. In a class of the embodiment, the implant drug delivery systems described herein are capable of releasing 4'-ethynyl-2-fluoro-2'-deoxyadenosine anhydrate resulting in a plasma concentration of 4'-ethynyl-2-fluoro-2'-deoxyadenosine between 0.02-15.0 ng/mL per day. In a further class of the embodiment, the implant drug delivery systems described herein are capable of releasing 4'-ethynyl-2-fluoro-2'-deoxyadenosine anhydrate resulting in a plasma concentration of 4'-ethynyl-2-fluoro-2'-deoxyadenosine between 0.02-8.0 ng/mL per day. In a subclass of the embodiment, the implant drug delivery systems described herein are capable of releasing 4'-ethynyl-2-fluoro-2'-deoxyadenosine anhydrate resulting in a plasma concentration of 4'-ethynyl-2-fluoro-2'-deoxyadenosine between 0.1-1.0 ng/mL per day.

The following examples are given for the purpose of illustrating the present invention and shall not be construed as being limitations on the scope of the invention.

Example 1

Monohydrate Crystalline Form MH of EFDA

Suitable starting quantities of Form MU of EFdA may be obtained by the synthetic process described in U.S. Pat. No. 7,339,053.

As those skilled in the art will appreciate, the use of seed crystal in the preparation of the anhydrate form as described in Example 3 is not initially required but is used for optimal production after initial quantities of the crystalline anhydrate form is produced.

Example 2

Anhydrate Crystalline Form of EFDA

Anhydrate crystalline EFdA form was prepared by premixing 0.396 g of water ($H_2O$) with acetonitrile (MeCN) to a total solvent weight of 31.66 g. EFdA Form MH (monohydrate) (2.83 g) and 31.02 g of the MeCN/$H_2O$ solvent mixture was added to a clean reactor. The resulting slurry was stirred at 25 °C for 5 minutes and then heated to 35 °C over 30 minutes and then 40 °C over 30 minutes. After stirring at 40 °C for 45 minutes, the slurry was heated to 50 °C over 2 hrs and then stirred at 50 °C for 1 hr. After the 1 hr age at 50 °C, the slurry was cooled to 25 °C over 8 hrs. The resulting slurry was filtered and dried by passing nitrogen ($N_2$) through the cake at ambient temperature for 24 hrs. Anhydrate EFdA form was collected. This anhydrate crystalline form can also be referred to as Anhydrate Crystalline Form 4 of EFdA.

Example 3

Anhydrate Crystalline Form of EFDA

Anhydrate Crystalline EFdA, also known as Form 4, was prepared using the critical water activity data by exploiting the control of super-saturation by slowly heating a slurry of the monohydrate in a system with a water amount slight below the critical water activity. The Form 4 preparation was done by premixing 0.9134 g of water and 73.07 g of acetonitrile in a bottle. 60.03 g of the acetonitrile/water mixture and 7.82 g of EFDA monohydrate were added to a clean vessel. The suspension was stirred for 30 minutes at 25 °C. Following a 30 minute age period, 0.80 g of EFDA Form 4 seed was added and the suspension was stirred for 30 minutes at 25.0 °C. The suspension was heated to 55 °C linearly over 10 hrs. 42.5 ml of acetonitrile was added to the slurry linearly over 2 hrs while stirring at 55 °C. At the end of the acetonitrile addition, the slurry was stirred for 1 hr at 55 °C. The slurry was then cooled to 25.0 °C nearly over 4 hrs and stirred for an additional 2 hrs at 25 °C. The slurry was filtered and washed with 20 ml of acetonitrile and dried by sucking nitrogen through the cake for 24 hrs at ambient temperature. EFDA Form 4 was collected.

Example 4

Preparation of Implant Drug Delivery Systems Containing 60 Wt % 4'-Ethynyl-2-Fluoro-2'-Deoxyadenosine Anhydrate and a Radiopaque Agent Implants were prepared using an extrusion process. Milled hydrophobic, aliphatic thermoplastic polyurethane and 4'-ethynyl-2-fluoro-2'-deoxyadenosine, anhydrate form, were blended with 60 wt % drug and 10 wt % Barium Sulfate as a radiopaque agent. The preblend was melt extruded with a twin screw extruder at temperatures ranging from 100-160 °C, screw speed at 20-30 rpm, and then pelletized. The pellets were then sieved and lubricated, then formed the core inside a diffusional barrier of hydrophilic, swelling thermoplastic polyurethane of 5% or 10% nominal water uptake prepared by co-extrusion with two single-screw extruders with temperatures ranging from 130-160 °C, and screw speed at 20-25 rpm to form a 2±0.05 mm diameter filament, with 0.05-0.25 mm diffusional barrier thickness, and then cut to a length of 40±2 mm.

The in vitro release rate of 4'-ethynyl-2-fluoro-2'-deoxyadenosine was determined using an ARCS (Automated Controlled Release System). The full implant was put into a 3D printed sample holder and was submerged in 50 mL of phosphate buffered saline (PBS) in a glass vessel. A temperature of 37 °C was maintained by a water bath. Samples were stirred by the system with magnetic stir bars set at 750 rpm. The volume of PBS was sufficient to maintain sink conditions. Sink conditions are defined as the drug concentration maintained at or below ⅓ of the maximum solubility (drug concentration ≤0.45 mg/mL in PBS at 37 °C). The ARCS removed a 1 mL sample once per day and filled it into an HPLC vial. A full media (50 mL) replacement was performed every day (24 h) by the system. Samples were assayed by HPLC (Waters Alliance 2695). Analysis of a 6 μL volume was performed at 262 nm with an Eclipse XDB-C8 column (150×4.6 mm, 5 μm) maintained at 40 °C. The mobile phase was 0.1% $H_3PO_4$ and 50:50 ACN:MeOH (75:25 v/v) at a flow rate of 1.5 mL/min.

To determine degradation of 4'-ethynyl-2-fluoro-2'-deoxyadenosine by HPLC, a 6 μL volume was injected onto a Water Atlantis T3 column (150×4.6 mm, 3 μm) maintained at 40 °C. The mobile phase was 0.1% TFA in Water and 0.1% TFA in 50:50 (v/v) ACN:MeOH with a flow rate of 1.5 mL/min. The mobile phase gradient is shown in the table below.

TABLE 1

4'-ethynyl-2-fluoro-2'-deoxyadenosine chemical stability HPLC method details

| Time (min) | 0.1 TFA in Water |
|---|---|
| 0.0 | 100 |
| 15.0 | 92 |
| 30.0 | 70 |
| 40.0 | 10 |
| 40.1 | 100 |
| 45.0 | 100 |

TABLE 2

4'-ethynyl-2-fluoro-2'-deoxyadenosine in vitro release from 60 wt % 4'-ethynyl-2-fluoro-2'-deoxyadenosine in LM-TPU implants with a 250 μm or 200 μm PU skin at sink conditions: reported as a % release from total [avg = average and std dev = standard deviation]

| | 60 wt % EFdA in LM-TPU + 250 μm PU skin | | 60 wt % EFdA in LM-TPU + 200 μm PU skin | |
|---|---|---|---|---|
| Time (days) | avg (%) | std. dev. | avg (%) | std. dev. |
| 1 | 0.6 | 0.1 | 0.5 | 0.0 |
| 2 | 0.9 | 0.1 | 0.8 | 0.1 |
| 3 | 1.1 | 0.1 | 1.1 | 0.1 |
| 4 | 1.3 | 0.1 | 1.3 | 0.1 |
| 7 | 1.9 | 0.1 | 1.9 | 0.1 |
| 14 | 3.0 | 0.2 | 2.9 | 0.1 |
| 21 | 3.9 | 0.2 | 3.8 | 0.2 |
| 29 | 4.9 | 0.2 | 4.8 | 0.2 |
| 35 | 5.6 | 0.2 | 5.4 | 0.2 |
| 42 | 6.2 | 0.3 | 6.1 | 0.2 |
| 49 | 6.9 | 0.3 | 6.6 | 0.2 |
| 56 | 7.5 | 0.3 | 7.1 | 0.3 |

TABLE 2-continued

4'-ethynyl-2-fluoro-2'-deoxyadenosine in vitro release from 60 wt % 4'-ethynyl-2-fluoro-2'-deoxyadenosine in LM-TPU implants with a 250 μm or 200 μm PU skin at sink conditions: reported as a % release from total [avg = average and std dev = standard deviation]

| | 60 wt % EFdA in LM-TPU + 250 μm PU skin | | 60 wt % EFdA in LM-TPU + 200 μm PU skin | |
|---|---|---|---|---|
| Time (days) | avg (%) | std. dev. | avg (%) | std. dev. |
| 63 | 8.0 | 0.3 | 7.5 | 0.4 |
| 70 | 8.5 | 0.4 | 8.0 | 0.4 |
| 78 | 8.2 | 0.5 | 9.0 | 0.3 |
| 84 | 8.7 | 0.6 | 9.5 | 0.3 |
| 91 | 9.0 | 0.6 | 10.0 | 0.3 |
| 98 | 9.5 | 0.6 | 10.5 | 0.3 |
| 106 | 10.0 | 0.6 | 11.0 | 0.3 |
| 114 | 10.3 | 0.6 | 11.4 | 0.3 |
| 121 | 10.7 | 0.7 | 11.8 | 0.3 |
| 128 | 11.1 | 0.7 | 12.2 | 0.3 |
| 135 | 11.4 | 0.7 | 12.6 | 0.3 |
| 142 | 11.8 | 0.7 | 13.0 | 0.3 |
| 149 | 12.1 | 0.8 | 13.4 | 0.3 |
| 165 | 12.9 | 0.8 | 14.2 | 0.3 |
| 179 | 13.5 | 0.9 | 14.9 | 0.3 |
| 199 | 14.5 | 0.9 | 16.0 | 0.3 |
| 255 | 16.9 | 1.1 | 18.6 | 0.4 |
| 259 | 17.0 | 1.1 | 18.8 | 0.4 |
| 301 | 18.4 | 1.2 | 20.3 | 0.5 |
| 344 | 20.0 | 1.3 | 22.0 | 0.5 |
| 377 | 21.3 | 1.4 | 23.4 | 0.5 |

LM-TPU—Low Melting Thermoplastic PolyUrethane
PU—PolyUrethane

TABLE 3

4'-ethynyl-2-fluoro-2'-deoxyadenosine in vitro release rates from 60 wt % 4'-ethynyl-2-fluoro-2'-deoxyadenosine in LM-TPU implants with a 250 μm or 200 μm PU skin

| Sample | Release Rate at day 30 (mg/day) | Release rate at day 60 (mg/day) | Release rate at day 90 (mg/day) | Release rate at 6 months (mg/day) |
|---|---|---|---|---|
| 60 wt % EFdA in LM-TPU + 250 μm PU skin | 0.07 | 0.04 | 0.03 | 0.03 |
| 60 wt % EFdA in LM-TPU + 200 μm PU skin | 0.07 | 0.04 | 0.03 | 0.03 |

Example 5

Preparation of Implant Drug Delivery Systems Containing 60 Wt % 4'-Ethynyl-2-Fluoro-2'-Deoxyadenosine Anhydrate and a Radiopaque Agent Implants were prepared using an extrusion or injection molding process. The milled polymer, and 4'-ethynyl-2-fluoro-2'-deoxyadenosine, anhydrate form, were blended at 60 wt % drug in hydrophobic, aliphatic thermoplastic polyurethane and 10 wt % Barium Sulfate as a radiopaque agent. The preblend was melt extruded with a twin screw extruder at temperatures ranging from 100-160 °C, screw speed at 20-30 rpm, and then pelletized. The pellets were then sieved and lubricated, then extruded or molded to form cores. The cores were then placed in pre-manufactured tubes or sheets of hydrophilic, swelling thermoplastic polyurethane of 5% or 10% nominal water uptake. The tubes or sheets were compression molded or sealed and trimmed, then cut to a length of 40±2 mm.

Example 6

Preparation of Implant Drug Delivery Systems Containing 60 Wt % 4'-Ethynyl-2-Fluoro-2'-Deoxyadenosine Anhydrate and a Radiopaque Agent Implants are prepared using an extrusion or injection molding process. The milled polymer, and 4'-ethynyl-2-fluoro-2'-deoxyadenosine, anhydrate form, are blended at 60 wt % drug in hydrophobic, aliphatic thermoplastic polyurethane and 10 wt % Barium Sulfate as a radiopaque agent. The preblend is melt extruded with a twin screw extruder at temperatures ranging from 100-160 °C, screw speed at 20-30 rpm, and then pelletized. The pellets are then sieved and lubricated, then extruded or molded to form cores. The cores are then placed in an injection molder and overmolded with hydrophilic, swelling thermoplastic polyurethane of 5% or 10% nominal water uptake, then cut to a length of 40±2 mm, if necessary

Counterexample 1

Preparation of Implant Drug Delivery Systems Containing 70 Wt % 4'-Ethynyl-2-Fluoro-2'-Deoxyadenosine Anhydrate and a Radiopaque Agent The milled polymer, and 4'-ethynyl-2-fluoro-2'-deoxyadenosine, anhydrate form, were blended at 70 wt % drug in hydrophobic, aliphatic thermoplastic polyurethane and 10 wt % Barium Sulfate as a radiopaque agent. The preblend was melt extruded with a twin screw extruder at temperatures ranging from 100-180 °C, screw speed at 20-30 rpm, but could not be successfully processed due to high die pressure and screw torque.

Counterexample 2

Preparation of Implant Drug Delivery Systems Containing 60 Wt % 4'-Ethynyl-2-Fluoro-2'-Deoxyadenosine Monohydrate and a Radiopaque Agent The milled polymer, and 4'-ethynyl-2-fluoro-2'-deoxyadenosine, monohydrate form, were blended at 60 wt % drug in hydrophobic, aliphatic thermoplastic polyurethane and 10 wt % Barium Sulfate as a radiopaque agent. The preblend was melt extruded with a twin screw extruder at temperatures ranging from 100-180 °C, screw speed at 20-30 rpm, but could not be successfully processed due to high die pressure and screw torque.

Counterexample 3

Preparation of Implant Drug Delivery Systems Containing 60 Wt % 4'-Ethynyl-2-Fluoro-2'-Deoxyadenosine Monohydrate and a Radiopaque Agent with Eva 9

The milled polymer, and 4'-ethynyl-2-fluoro-2'-deoxyadenosine, monohydrate form, were blended at 70 wt % drug in polyethylene vinyl acetate, 9% vinyl acetate (EVA 9) and 10 wt % Barium Sulfate as a radiopaque agent. The preblend was melt extruded with a twin screw extruder at temperatures ranging from 100-180 °C, screw speed at 20-30 rpm, but could not be successfully processed due to apparent degradation of the API and discoloration of the formulation.

Counterexample 4

Preparation of Implant Drug Delivery Systems Containing 60 Wt % 4'-Ethynyl-2-Fluoro-2'-Deoxyadenosine Monohydrate and a Radiopaque Agent with Eva 28+Hydrophilic TPU Diffusional Barrier Implants were prepared using an extrusion process. The milled polymer, and 4'-ethynyl-2-fluoro-2'-deoxyadenosine, monohydrate form, were blended at 60 wt % drug in polyethylene vinyl acetate, 28% vinyl acetate (EVA 28) and 10 wt % Barium Sulfate as a radiopaque agent. The preblend was melt extruded with a twin screw extruder at temperatures ranging from 100-160 °C, screw speed at 20-30 rpm, and then pelletized. The pellets were then sieved and lubricated, then formed the core inside a diffusional barrier of hydrophilic, swelling thermoplastic polyurethane of 5% nominal water uptake prepared by co-extrusion with two single-screw extruders with temperatures ranging from 130-160 °C, and screw speed at 20-25 rpm to form a 2±0.05 mm diameter filament, with 0.05-0.25 mm diffusional barrier thickness, and then cut to a length of 40±2 mm. Upon soaking these samples in phosphate buffer saline, the diffusional barriers expanded and delaminated in some cases, perhaps due to insufficient adhesion between the core and diffusional barrier.

What is claimed:

1. An implant drug delivery system comprising:

(a) a core comprising a biocompatible nonerodible polymer comprising thermoplastic poly (urethane) and a crystalline 4'-ethynyl-2-fluoro-2'-deoxyadenosine anhydrate, wherein the 4'-ethynyl-2-fluoro-2'-deoxyadenosine anhydrate is present in the core between 1% and 60% by weight, and (b) a biocompatible nonerodible diffusional barrier comprising a polymer, wherein said diffusional barrier has a thickness between 50 μm and 300 μm, wherein said implant drug delivery system is adapted for subdermal implantation, and 4'-ethynyl-2-fluoro-2'-deoxyadenosine anhydrate is continually released in vivo at a rate resulting in a plasma concentration of 4'-ethynyl-2-fluoro-2'-deoxyadenosine between 0.02 ng/ml and 300.0 ng/ml for a period of six months to thirty-six months.

2. The implant drug delivery system of claim 1 wherein the 4'-ethynyl-2-fluoro-2'-deoxyadenosine plasma concentration is between 0.02 ng/ml and 30.0 ng/mL.

3. The implant drug delivery system of claim 2 wherein the 4'-ethynyl-2-fluoro-2'-deoxyadenosine plasma concentration is between 0.02 ng/ml and 8.0 ng/mL.

4. The implant drug delivery system of claim 1 wherein the 4'-ethynyl-2-fluoro-2'-deoxyadenosine anhydrate is present in the core between 10% and 60% by weight.

5. The implant drug delivery system of claim 4 wherein the 4'-ethynyl-2-fluoro-2'-deoxyadenosine anhydrate is present in the core between 40% and 60% by weight.

6. The implant drug delivery system of claim 4 wherein the 4'-ethynyl-2-fluoro-2'-deoxyadenosine anhydrate is present in the core at about 40% by weight.

7. The implant drug delivery system of claim 4 wherein the 4'-ethynyl-2-fluoro-2'-deoxyadenosine anhydrate is present in the core at about 60% by weight.

8. The implant drug delivery system of claim 1, wherein the diffusional barrier comprises a hydrophilic polymer or a hydrophobic polymer with a soluble filler.

9. The implant drug delivery system of claim 8, wherein the diffusional barrier comprises a polymer selected from the group consisting of ethylene vinylacetate copolymer (EVA), silicone, crosslinked poly(vinyl alcohol), unplasticized polyvinyl chloride, crosslinked homopolymers of polyvinyl acetate, crosslinked copolymers of polyvinyl acetate, crosslinked polyesters of acrylic acid, crosslinked polyesters of methacrylic acid, polyvinyl alkyl ethers, polyvinyl fluoride, polycarbonate, polyamide, polysulphones, styrene acrylonitrile copolymers, crosslinked poly(ethylene oxide), poly (alkylenes), poly(vinyl imidazole), poly(ethylene terephthalate), poly(urethane), poly(hydroxy ethylmethacrylate), acyl substituted cellulose acetates, partially hydrolyzed alkylene-vinyl acetate copolymers, completely hydrolyzed alkylene-vinyl acetate copolymers, poly(esters), polyphosphazenes, chlorosulphonated polylefins, and combinations thereof.

10. The implant drug delivery system of claim 8, wherein the diffusional barrier comprises poly(urethane).

11. The implant drug delivery system of claim 10, wherein the poly(urethane) has a water uptake of between 1% and 20% by weight.

12. The implant drug delivery system of claim 8, wherein the diffusional barrier comprises hydrophilic thermoplastic poly(urethane).

13. The implant drug delivery system of claim 1 wherein the diffusional barrier has a thickness between 50 82 m and 200 μm.

14. The implant drug delivery system of claim 1, wherein the core and the biocompatible nonerodible diffusional barrier are prepared by co-extrusion, and the co-extrusion is carried out at a temperature between 130 °C and 190 °C.

15. The implant drug delivery system of claim 14 wherein the co-extrusion is carried out at a temperature between 130 ° C and 160 °C.

16. The implant drug delivery system of claim 1 wherein the 4'-ethynyl-2-fluoro-2'-deoxyadenosine anhydrate is characterized by a powder x-ray diffraction pattern with at least peaks at diffraction angles degrees 2 theta (+/−0.2°) 11.79, 12.39, 14.70 and 15.51 in a powder x-ray diffraction obtained using Cu K alpha radiation.

17. The implant drug delivery system of claim 1 comprising between 1% and 20% by weight of a radiopaque material.

18. The implant drug delivery system of claim 17 wherein the radiopaque material is barium sulfate.

19. The implant drug delivery system of claim 1 wherein the 4'-ethynyl-2-fluoro-2'-deoxyadenosine is released at therapeutic concentrations for a duration from between twenty-four months and thirty-six months.

20. An implant drug delivery system comprising:

(a) a core comprising a biocompatible nonerodible polymer comprising thermoplastic poly(urethane) and a crystalline 4'-ethynyl-2-fluoro-2'-deoxyadenosine anhydrate, which is present in the core between 1% and 60% by weight, and (b) a biocompatible nonerodible diffusional barrier comprising a polymer, wherein said diffusional barrier has a thickness between 50 μm and 300 μm, wherein said 4'-ethynyl-2-fluoro-2'-deoxyadenosine anhydrate has an in vitro release rate of 0.03 to 0.07 mg/day when measured between one and six months following implantation.

21. The implant drug delivery system of claim 20 wherein the core and the biocompatible nonerodible diffusional barrier both comprise poly(urethane).

22. The implant drug delivery system of claim 20 wherein 4'-ethynyl-2-fluoro-2'-deoxyadenosine anhydrate has an in vitro release rate of 0.07 mg/day when measured at day 30 following implantation.

23. The implant drug delivery system of claim 20 wherein 4'-ethynyl-2-fluoro-2'-deoxyadenosine anhydrate has an in vitro release rate of 0.04 mg/day when measured at day 60 following implantation.

24. The implant drug delivery system of claim 20 wherein 4'-ethynyl-2-fluoro-2'-deoxyadenosine anhydrate has an in vitro release rate of 0.03 mg/day when measured at six months following implantation.

* * * * *